United States Patent [19]

Hirono et al.

[11] 3,967,951
[45] July 6, 1976

[54] SELECTIVE HERBICIDES

[75] Inventors: Yoshihiko Hirono, Hiratsuka; Hisao Ishikawa, Oiso; Shozo Yamada, Hiratsuka; Saburo Kano; Osami Nomura, both of Odawara, all of Japan

[73] Assignee: Nippon Soda Company Limited, Tokyo, Japan

[22] Filed: Jan. 31, 1974

[21] Appl. No.: 438,475

[30] Foreign Application Priority Data
Feb. 5, 1973  Japan.................................. 48-13768

[52] U.S. Cl.................................... 71/90; 260/305
[51] Int. Cl.².............................................. A01N 9/12
[58] Field of Search....................................... 71/90

[56] References Cited
UNITED STATES PATENTS
3,714,177  1/1973  Engelhart.................................. 71/90
3,725,428  4/1973  Janiak..................................... 260/305

FOREIGN PATENTS OR APPLICATIONS
1,085,430  10/1967  United Kingdom..................... 71/90

Primary Examiner—Glennon H. Hollrah
Attorney, Agent, or Firm—George B. Oujevolk

[57] ABSTRACT

A selective herbicidal composition comprising an effective amount of a compound of the formula

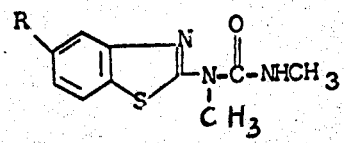

wherein R is selected from the group consisting of isopropyl and tertbutyl.

5 Claims, No Drawings

SELECTIVE HERBICIDES

The present invention relates to novel compounds, herbicidally active compositions and to a method of combating weeds.

It is an object of the present invention to prepare selective herbicidal compositions and method for killing undesired plants. Another object is to prepare formulations showing selective activity as pre-emergent and post-emergent herbicides.

It has been found that the compositions of the present invention possess superior selective herbicidal activity. The compounds of the present invention have the following chemical formula

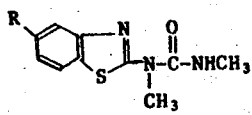

wherein R is selected from the group consisting of ispropyl and tert-butyl.

It is already known that 1,3-dimethyl-1-(2-benzothiazolyl)-urea has strong herbicidal properties as shown in U.S. Pat. No. 2,756,135 and British Pat. No. 1,085,430. It exhibits selective herbicidal properties when it is used in cotton, wheat and barley cultivation; however it cannot be used for selective weed control in rice cultivation because it has strong herbicidal activity in soil treatment and phytotoxicity for rice plant. Moreover, when it is applied after emergence in wheat cultivation, in which the weeds have already grown to a substantial height, it is difficult to perfectly control such weeds without damage to the cultivated plants.

And it has been disclosed in Offenlegungsschrift P 2150107.5 that 1,3-dimethyl-1-[2-(5-methylbenzothiazolyl)]urea is highly selective in wheat cultivation and kills only weeds, even when both the weeds and wheat have grown. But it cannot be used in rice cultivation because there is heavy phytotoxicity to rice plant the same as 1,3-dimethyl-1-(2-benzothiazolyl)urea.

The inventors synthesized various benzothiazolylureas and examined the herbicidal activity thereof, and have discovered that 1,3-dimethyl-1-(2-benzothiazolyl)urea having at the 5 position of the benzothiazol ring a substituent such as isopropyl or tert-butyl group is very suitable for selective weed control in rice cultivation.

Namely, the compound of the present invention does not damage rice plant, whereas it completely destroys annual weeds such as barnyard grass, monochoria, cyperus etc. and perennial weeds such as flatstage, slender spikerush etc.

It goes without saying that the compounds of the present invention exhibit superior activity against barnyard grass (*Echinchloa oryzicola*). chickweed (*Stellaria neglecta*), common purslane (*Portulaca oleracea*), common sow thistle (*Souchus oleraceus*), green foxtail (*Setaria viridis*), large crab-grass (*Degitaria adscendens*), smooth pigweed (*Chenopodium album*) and others in foliar spray. Furthermore, these compounds exhibit special high selectivity in the application in wheat, barley and cotton cultivation, even if such application is carried out at any steps of growth of the weeds the same as 1,3-dimethyl-1-(2-benzothiazolyl)-urea.

Consequently, the compounds of the present invention can be used for controlling weeds not only in wheat cultivation, but also in rice cultivation, because there is no fear for phytotoxicity to rice plant and wheat.

It is another advantage that the compounds of the present invention have low toxicity for warm blooded animals and fish.

The compound of this invention, for example, can be prepared by the reaction illustrated below.

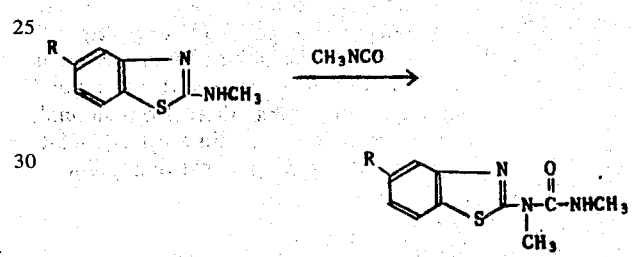

The reaction can be usually carried out in a proper inert solvent such as acetone, alcohol, ether, benzene, etc., at a temperature from 0°C to the boiling point of the solvent employed, preferably in the presence of triethylamine, for an adequate time according to the other reaction conditions. At the end of the reaction, an objective product is isolated from the reaction mixture by conventional techniques. For example, the reaction mixture may be poured into water, or water may be added thereto. The precipitated materials are separated from the aqueous solution by filtration. Instead of the above, the solvent may be distilled off from the reaction mixture under reduced pressure. The separated compound may be further washed with water, if necessary, and purified by recrystallizing from an organic solvent such as acetone, alcohol, etc.

The above starting material can be prepared in accordance with the following equations:

(1)

(2)

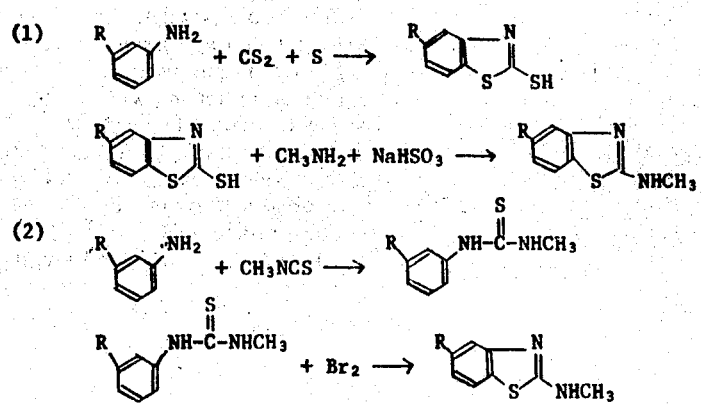

In case that R of the formula of meta-alkylaniline in the above equations (1) and (2) is a methyl group, it is very difficult to obtain only 5-methyl-(2-methylamino)benzothiazole because the 7-methyl-(2-methylamino)benzothiazole as the by-product is often obtained.

But, when R is isopropyl or tert-butyl group, only 5-isopropyl or tert-butyl-(2-methylamino)benzothiazole is obtained since 7-isopropyl or tert-butyl-(2-methylamino)benzothiazole is seldom obtained due to steric hindrance of isopropyl or tert-butyl group.

The methods of preparing typical compounds of the present invention is illustrated by the following examples.

EXAMPLE 6

Preparation of 1,3-dimethy-1-[2-(5-t-butylbenzothiazolyl)]urea 22g of 5-t-butyl-(2-methylamino)benzothiazole was dissolved in 70ml of acetone, a few drops of triethylamine was added dropwise to acetone solution, and to which, 6.3g of methylisocyanate was added gradually under agitation. Agitation was continued at room temperature for 15 minutes. Then, the reaction mixture was poured into about 200 ml. of water to precipitate the objective substance. The precipitated materials were collected by filtration, washed with water, and dried. Said materials were recrystallized from alcohol, and 21.8g of white crystals of 1,3-dimethyl-1-[2-(5-t-butylbenzothiazolyl)]urea having a melting point of 109°-110°C was obtained.

EXAMPLE 2

Preparation of 1,3-dimethyl-1-[2-(5-isopropylbenzothiazolyl)]urea 20.5g of 2-methylamino-5-isopropylbenzothiazole were dissolved in 70ml of acetone, a few drops of triethylamine were added dropwise to the acetone solution and to which 20g of methylisocyanate was added gradually under agitation. The reaction mixture was refluxed for 15 minutes.

Then, the reaction mixture was poured into about 200ml of water to precipitate the objective substance. The precipitated materials were collected by filtration, washed with water, and dried. Said materials were recrystallized from alcohol, and 20g of white crystals of 1,3-dimethyl-1-[2-(5-isopropylbenzothiazolyl)]urea having a melting point of 99°-101°C was obtained.

In this invention, it is desirable that a proper quantity of active ingredient of more than 30g per 10 are, preferably 50–100g per 10 are ("are" is "100 square meters"), is selectively used in accordance with the kind of subject plants, the method of application and the kind of composition. The compound may be applied to the plants or soils as it is or as a wettable powder, an emulsifiable concentrate, a dust formulation, a granular formulation or others in a form generally used in pesticidal compositions which is made by mixing with suitable carriers. As solid carriers, talc, bentonite, clay, diatomaceous earth, vermiculite, etc. are used. As liquid carriers, water, alcohol, benzene, xylene, cyclohexane, cyclohexanone, kerosine, dimethylformamide, dimethylsulfoxide, etc. are used. For instance, a wettable powder or an emulsifiable concentrate containing the proper quantity of the active compound is suspended or emulsified in water and then sprayed on the foliages of the weeds or on the soil around the cultivated plants. Furthermore, the compound may be used as a mixture with known herbicides such as triazine derivatives, thiolcarbamate derivatives, and others.

Some examples in this invention are stated below. But the main compounds and the additives are not intended to be limited by these Examples.

EXAMPLE 3

Wettable Powder

| | Parts by weight |
|---|---|
| 1,3-dimethyl-1-[2-(5-isopropylbenzothiazolyl)]-urea | 70 |
| Sodium alkylsulfonate | 6 |
| Diatomaceous earth | 24 |

These are mixed homogeneously and micronized to fine particles. As a result, a wettable powder containing 70% of the active ingredient is obtained. In practical use, it is diluted to a certain concentration with water and is sprayed as a suspension.

EXAMPLE 4

Emulsifiable Concentrate

| | Part by weight |
|---|---|
| 1,3-dimethyl-1-[2-(5-tert-butylbenzothiazolyl]urea | 40 |
| Polyoxyethylene phenyl ether | 5 |
| Xylene | 35 |
| Dimethylformamide | 20 |

These are mixed and dissolved. As a result, an emulsifiable concentration containing 40% of the active ingredient is obtained. In practical use, it is diluted to a certain concentration with water and then is sprayed as an emulsion.

EXAMPLE 5

Dust Formulation

| | Part by weight |
|---|---|
| 1,3-dimethyl-1-[2-(5-tert-butylbenzothiazolyl)]urea | 10 |
| Talc | 38 |
| Clay | 37 |
| Bentonite | 10 |
| Sodium alkylsulfate | 5 |

These are mixed homogeneously, micronized to fine particles, and, as a result a dust formulation containing 10% of the active ingredient is obtained. In practical use, it is directly applied.

The superior selective herbicidal effect of compounds of this invention are clearly illustrated by the following tests.

As a compound for the comparison, 1,3-dimethyl-1-(2-benzothiazolyl)urea and 1,3-dimethyl-1-[2-(5-methylbenzothiazolyl)]urea were employed.

TEST 1.

Soil was packed to a depth of 1cm in a pot 9cm in diameter and 6cm deep, and 60 seeds of rice plant and barnyard grass were sown in it and covered slightly with soil. Said pot was filled with water when the test plants were grown to 1 and 3 leaf-stage.

Then, dust formulation, prepared as in Example 5 were applied to the surface of the soil.

After 14 days, the degrees of damage to the test plants were observed and evaluated by the values 0–5 which have the following meaning.
0: no effect
1: a few slightly burnt spots
2: marked damage to leaves
3: some leaves and parts of stalks partially dead
4: plant partially destroyed
5: plant completely destroyed or no germination
The results were shown in Table 1.

Table 1

| Test compound | Application rate (g/10are) | Test plant | | | |
|---|---|---|---|---|---|
| | | 1st leaf-stage | | 3rd leaf-stage | |
| | | Rice plant | Barnyard grass | Rice plant | Barnyard grass |
| 1,3-dimethyl-1-[2-(5-isopropylbenzothiazolyl)]-urea | 1,000 | 1 | 5 | 1 | 5 |
| | 500 | 0 | 5 | 0 | 5 |
| | 250 | 0 | 5 | 0 | 5 |
| | 125 | 0 | 5 | 0 | 4 |
| 1,3-dimethyl-1[2-(5-tert-butylbenzothiazolyl)]urea | 1,000 | 0 | 5 | 0 | 5 |
| | 500 | 0 | 5 | 0 | 5 |
| | 250 | 0 | 5 | 0 | 5 |
| | 125 | 0 | 5 | 0 | 4 |
| 1,3-dimethyl-1-(2-benzothiazolyl)-urea | 1,000 | 5 | 5 | 4 | 5 |
| | 500 | 5 | 5 | 2 | 5 |
| | 250 | 4 | 5 | 2 | 3 |
| | 125 | 3 | 3 | 1 | 1 |

TEST 2

Test compounds were formulated to wettable powders in similar manner to that of Example 3, aqueous suspensions were prepared by diluting wettable powders and they were sprayed on leaves and stems of upland rice and barnyard grass in vats having 780cm$^2$.

After 21 days, the degrees of the damage to the test plants were observed and evaluated by the values 0–5 which have the same meanings of those of Test 1. The results were shown in Table 2.

Table 2

| Test compound | Concentration (ppm) | Upland Rice | Barnyard Grass |
|---|---|---|---|
| 1,3-dimethyl-1-[2-(5-isopropylbenzothiazolyl)]-urea | 500 | 0 | 5 |
| | 250 | 0 | 5 |
| | 125 | 0 | 5 |
| 1,3-dimethyl-1-[2-(5-tert-butylbenzothiazolyl)]urea | 500 | 0 | 5 |
| | 250 | 0 | 5 |
| | 125 | 0 | 5 |
| 1,3-dimethyl-1-(2-benzothiazolyl)-urea | 500 | 4 | 5 |
| | 250 | 3 | 5 |
| | 125 | 2 | 4 |

TEST 3

Field-Test

A 70% wettable powder of 1,3-dimethyl-1-[2-(5-tert-butylbenzothiazolyl)]urea of this invention was prepared in similar manner to that of Example 3 and diluted to a certain concentration with water.

The resulting aqueous suspension were sprayed when wheat and weeds were grown to the following stages:

| Test plant | Stage | Abbreviation |
|---|---|---|
| wheat | 3.5 leaf | —40 |
| annual bluegrass (Poa annua) | begining of tillering | P.a. |
| water foxtail (Alopecurus aequalis) | " | A.a. |
| common chickweed (Stellaria media) | begining of blossom | S.m. |
| henbit (Lamium amplexicaule) | " | L.a. |
| spherpherd's purse (Capsella bursa) | " | C.b. |
| cleavers (Galium aparine) | " | G.a. |
| (Cerastium arvense) | " | C.a. |
| byzantine speedwell (Veronica persica) | " | V.p. |

After 50 days, the degrees of the damages to the test plants were observed and evaluated by the same meanings of those of Test 1.

The results were shown in Table 3.

Table 3

| Test compound | Quantities of the compound (g. of active ingredient/ha) | Test plant | | | | | | | | |
|---|---|---|---|---|---|---|---|---|---|---|
| | | wheat | P.a. | A.a. | S.m. | L.a. | C.b. | G.a. | C.a. | V.p. |
| 1,3-dimethyl-1-[2-(5-tert-butylbenzothiazolyl)]urea | 1,000 | 1 | 4 | 4 | 5 | 5 | 5 | 5 | 5 | 5 |
| | 500 | 0 | 1 | 0 | 5 | 5 | 5 | 4 | 5 | 5 |

Table 3-continued

| Test compound | Quantities of the compound (g. of active ingredient/ha) | wheat | P.a. | A.a. | S.m. | Test plant L.a. | C.b. | G.a. | C.a. | V.p. |
|---|---|---|---|---|---|---|---|---|---|---|
| 1,3-dimethyl-1-[2-(5-methyl-benzothiazolyl)]urea | 1,000 | 0 | 0 | 1 | 5 | 5 | 4 | 2 | 4 | 0 |
|  | 500 | 0 | 0 | 1 | 4 | 4 | 5 | 0 | 0 | 0 |

COMPARATIVE EXAMPLE ACCORDING TO ABOVE EQUATION (1)

5-methyl-(2-mercapto)benzothiazole

In an autoclave of 3 liters, 963g of m-toluidine, 820g of carbon disulfide and 288g of sulfur were placed, the reaction was carried out at the temperature of 220° ~ 230°C for 4 hours with stirring and the pressure in the autoclave was 50 kg/cm$^2$.

After cooling, 904g of 5-methyl-(2-mercapto)benzothiazole was obtained. (yield: 55.5%).

Simultaneously, 487g of 7-methyl-(2-mercapto)benzothiazole as by-product was obtained.

5-tert-butyl-(2-mercapto)benzothiazole

In a autoclave of 3 liters, 1341g of meta-tert-butylaniline, 820g of carbon disulfide and 288g of sulfur were placed, the reaction was carried out under the same conditions as above. After cooling, 1765g of 5-tert-butyl-(2-mercapto)benzothiazole was obtained. (yield: 88.3%)

7-tert-butyl-(2-mercapto)benzothiazole was not obtained at all.

COMPARATIVE EXAMPLE ACCORDING TO ABOVE EQUATION (2)

5-methyl-(2-methylamino)benzothiazole 28.2g of 1-(3-methylphenyl)-3-methylthiourea were dissolved in 190g of chloroform and 2.5g of bromine was added to the chloroform solution at the temperature of 45° ~ 50°C for 30 minutes and the agitation was continued at 50° ~ 60°C for 5.5 hours.

After cooling, 21.1g of the crude HBr salt of 2-methylamino-benzothiazoles was obtained and poured into 420g of water and was agitated at the temperature of 70° ~ 80°C for 30 minutes.

After cooling to 50°C, the HBr salt of 5-methyl-(2-methylamino)benzothiazole was filtered and 8.6g of 5-methyl-(2-methylamino)benzothiazole was obtained after neutralization. (yield: 30.6%).

Simultaneously, 6.2g of 7-methyl-(2-methylamino)-benzothiazole as by-product were obtained through neutrailzation of above filtrate. (yield: 22.4%)

5-tert-butyl-(2-methylamino)benzothiazole

The same reaction procedures in the above were carried out by using 10g of 1-(3-tert-butylphenyl)-3-methylthiourea and 7.4g of bromine at the reaction temperature of 5° ~ 10°C, and thereby, 4.7g of 5-tert-butyl(2-methylamino)benzothiazole having a melting point of 160° ~ 164°C was obtained. (yield: 47%)

7-tert-butyl-(2-methylamino)benzothiazole was not obtained at all.

From the yield of the above Examples, it is apparent that a process for the production of a compound of this invention is superior.

What is claimed is:

1. A method of combating weeds which comprises applying to the weed habitat an effective amount of a compound of the formula

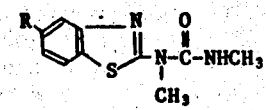

wherein R is selected from the group consisting of isopropyl and tert-butyl.

2. A method of combating weeds which comprises applying to the weed habitat an effective amount of 1,3-dimethyl-1-[2-(5-tert-butylbenzothiazolyl)]urea.

3. A method of combating weeds in rice or wheat cultivation, which comprises applying to the area of cultivation an effective amount of a compound of the formula

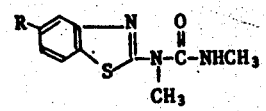

wherein R is selected from the group consisting of isopropyl and tert-butyl.

4. A selective herbicidal composition comprising an inert carrier and a herbicidally effective amount of a compound of the formula

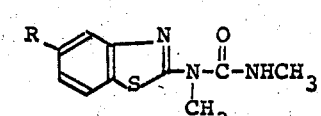

wherein R is selected from the group consisting of isopropyl and tert-butyl.

5. A selective herbicidal composition comprising an inert carrier and a herbicidally effective amount of 1,3-dimethyl-1-[2-(5-tert-butylbenzothiazolyl)]urea.

* * * * *